US005916778A

United States Patent [19]
Stone et al.

[11] Patent Number: 5,916,778
[45] Date of Patent: *Jun. 29, 1999

[54] DIAGNOSTICS BASED ON A GLAUCOMA CAUSING GENE

[75] Inventors: Edwin M. Stone, Iowa City; Val C. Sheffield, Coralville; Wallace L. M. Alward, Iowa City, all of Iowa

[73] Assignee: University of Iowa Research Foundation, Iowa City, Iowa

[ * ] Notice: This patent issued on a continued prosecution application filed under 37 CFR 1.53(d), and is subject to the twenty year patent term provisions of 35 U.S.C. 154(a)(2).

[21] Appl. No.: 08/234,218

[22] Filed: Apr. 28, 1994

[51] Int. Cl.$^6$ .............................. C12P 19/34; C12Q 1/68; C07H 21/04

[52] U.S. Cl. ...................... 435/91.2; 435/6; 536/24.31; 536/23.5

[58] Field of Search ........................ 435/6, 91.2, 172.3; 514/44; 536/23.5, 24.31

[56] References Cited

U.S. PATENT DOCUMENTS 4,683,195  7/1987  Mullis et al. ................................ 435/6

FOREIGN PATENT DOCUMENTS

WO 96/14411  5/1996  WIPO ............................ C12N 15/12

OTHER PUBLICATIONS

Orkin et al., Report and Recommendations of the Panel to Assess the NIH Investment in Research on Gene Therapy, Dec. 7, 1995.
Wax et al., Journal of Ocular Pharmacology, vol. 10, pp. 403–410, 1994.
Written opinion dated Oct. 23, 1988, PCT/US97/20702.
Database entry HSU85257, Mar. 2, 1997 (Nguyen et al.).
Escribano, J. et al. (1995) "Isolation and Characterization of Cell–Specific cDNA Clones from a Substractive Library of the Ocular Ciliary Body of a Single Normal Human Donor: Transcription and Synthesis of Plasma Proteins", *J. Biochem.*, 118:921–931.
Ortega, J. et al. (1997) "Cloning and Characterization of Subtracted cDNAs from a Human Ciliary Body Library Encoding TIGR, a Protein Involved in Juvenile Open Angle Glaucoma with Homology to Myosin and Olfactomedin", *FEBS Letters*, 413:349–353.
Stone, Edwin M. et al. (1997) "Identification of a Gene that Causes Primary Open Angle Glaucoma", *Science*, 275:668–670.
Sunden, Sara L.F. et al. (1996) "Fine Mapping of the Autosomal Dominant Juvenile Open Angle Glaucoma (GLC1A) Region and Evaluation of Candidate Genes" *Genome Res.*, 6:862–869; and.
International Search Report (PCT/US97/20702) Mar. 13, 1998.

"CHLC Report" (Newsletter), Cooperative Human Linkage Center, vol. 1 No. 1, pp. 1–18, May 1993.
"Editorial: Genetic associations of glaucoma" *British Journal of Ophthalmology*, vol. 64, pp. 225–226, 1980.
Cotton, P., "Glaucoma Gene Mapped to Chromosome 1" *JAMA*, vol. 269, No. 21, p. 2715, Jun. 2, 1993.
Francois, J., "Genetics and Primary Open–Angle Glaucoma" *Am. J. Ophthalmol.*, vol. 61, pp. 652–665, 1996.
Harris, D., "The Inheritance of Glaucoma: A Pedigree of Familial Glaucoma" *Am. J. Ophthalmol.*, vol. 60, pp. 91–95, 1965.
Johnson, A.T. et al., "Clinical Features and Linkage Analysis of a Family with Autosomal Dominant Juvenile Glaucoma" *Ophthalmology*, vol. 100, No. 4, pp. 524–528, Apr. 1993.
Kass, M.A. et al., "Histocompatibility Anitgens and Primary Open–Angle Glaucoma: A Reassessment" *Arch Ophthalmol*, vol. 96, pp. 2207–2208, Dec. 1978.
Kolker, A.E., Glaucoma Family Study: Ten–Year Follow–Up (Preliminary Report) *Israel J. Med. Sci.*, vol. 8, No. 8–9, pp. 1357–1361, Aug.–Sep. 1972.
Leighton, D.A., "Survey of the first–degree relatives of glaucoma patients" *Trans. ophthal. Soc. U.K.*, vol. 96, pp. 28–32, 1976.
Martin, J.P. and E.C. Zorab, "Familial glaucoma In nine generations of a South Hampshire family" *Brit. J. Ophthal.*, pp. 536–542, 1974.
Miller, S.J.H. and G.D. Paterson, "Studies on Glaucoma Relatives" *Brit. J. Ophthal.*, vol. 46, pp. 513–522, 1962.
Orita, M. et al., "Detection of polymorphisms of human DNA by gel electrophoresis as single–strand conformation polymorphisms" *Proc. Natl. Acad. Sci. USA*, vol. 86, pp. 2766–2770, Apr. 1989.
Perkins, E.S., "Family studies in glaucoma" *Brit. J. Ophthal.*, vol. 58, pp. 529–535, 1974.
Richards, J.E. et al., "Mapping of a Gene for Autosomal Dominant Juvenile–Onset Open–Angle Glaucoma to Chromosome Iq" *Am. J. Hum. Genet.*, vol. 54, pp. 62–70, 1994.
Sheffield, V.C. et al., "Attachment of a 40–base–pair G+C–rich sequence (GC–clamp) to genomic DNA fragments by the polymerase chain reaction results in improved detection of single–base changes" *Proc. Natl. Acad. Sci. USA*, vol. 86, pp. 232–236, Jan. 1989.
Sheffield, V.C. et al., "Genetic linkage of familial open angle glaucoma to chromosome 1q21–q31" *Nature Genetics*, vol. 4, pp. 47–50, May 1993.
Weatherill, J.R. and C.T. Hart, "Familial hypoplasia of the iris stroma associated with glaucoma" *Brit. J. Ophthal.*, vol. 53, pp. 433–438, 1969.

*Primary Examiner*—Deborah Crouch
*Assistant Examiner*—Jill D. Martin
*Attorney, Agent, or Firm*—Foley, Hoag & Eliot, LLP; Beth E. Arnold; Anita Varma

[57] ABSTRACT

Methods and compositions for glaucoma diagnostics are disclosed.

19 Claims, 3 Drawing Sheets

DIAGNOSTICS BASED ON A GLAUCOMA CAUSING GENE

GOVERNMENT SUPPORT

Work described herein has been supported, in part, by Public Health Service Research Grants EY08426, P50HG00835 and HG00457. The U.S. Government may therefore have certain rights in the invention.

BACKGROUND OF THE INVENTION

Glaucoma is a diverse group of disorders characterized by a damaged optic nerve with resultant loss of peripheral vision and ultimately loss of central vision. In most cases, an elevated intraocular pressure is felt to play a role in the visual loss. Glaucoma is the second leading cause of permanent blindness in the United States and the single leading cause of blindness among African-Americans (Leske, M. C. (1983) *American Journal of Epidemiology* 118:166–191; Francois, J. (1966) *Am J. Ophthalmol* 61:652–665; Hoskins, H. D. et al. (1989) *Sixth ed. St. Louis: C. V. Mosby*) Glaucoma developing between birth and age three is termed primary infantile glaucoma. The majority of cases of glaucoma develop in adulthood after age forty. Juvenile glaucoma occurs later than infantile glaucoma but earlier than the usual adult forms (Hoskins, H. D. et al (1989) *Sixth ed. St. Louis: C. V. Mosby*).

Infantile glaucoma is thought to be caused by incomplete development of the anterior segment of the eye. In contrast, there are no developmental anomalies associated with the more prevalent adult forms of glaucoma. Children with infantile glaucoma typically have symptoms of tearing, photophobia, corneal clouding and large eyes by the time they reach one year of age.

Juvenile open angle glaucoma occurs after age three (when the eye ceases to grow in response to increased intra-ocular pressure) but before age forty. There are two forms of juvenile glaucoma; one that appears as a late form of infantile glaucoma with similar iridocorneal angle anomalies, and another that has normal angles and is similar to adult primary open angle glaucoma.

The adult onset glaucomas are subdivided by the mechanisms of pressure elevation into closed angle and open angle glaucoma. If the trabecular meshwork (located in the angle between the iris and cornea) is free from mechanical obstruction, the glaucoma is termed primary open angle glaucoma (POAG). Adult primary open angle glaucoma accounts for about 60–70% of all cases of glaucoma (Hoskins, H. D. et al (1989) *Sixth ed. St. Louis: C. V. Mosby*). Population surveys suggest that the prevalence of primary open angle glaucoma in the general population is between 0.63% and 1.25% (Banks, J. L. K. et al. (1968) *British Medical Journal* 1:791; Popovic, V. (1982) *Acta Ophthalmologica* 60:745–758). In these patients, there is an insidious increase in intraocular pressure, usually beginning late in life. The anterior segment of the eye appears normal by examination and there is no identifiable cause of the increased pressure. When damage to the optic nerve or loss of visual field is detected, the patient is diagnosed as having glaucoma. In some forms of adult primary open angle glaucoma with iris hypoplasia (Weatherill, J. R. et al (1969) *Br J Ophthalmol* 53:433–8; Berg, F. (1932) *Acta Ophthalmol* 10:568–587; Francois, J. et al (1950) *Bull Soc Belge Ophthal* 96:665–683; Hambresin, M. L. et al (1946) *Societe Francaise d'Ophthalmologie* 59:219–223; McCulloch, C. et al (1950) *Transcripts of the Canadian Ophthalmologic Society* 79–91).

It has been reported that 4–16% of first degree relatives of patients with POAG develop the disease (Phelps, C. D. & Podos, S. M., Glaucoma: In Genetic and Metabolic Eye Diseases (ed. Goldberg, M. F.) 237–259 (Little Brown, Boston, 1974); Miller, S. J. H. & Paterson, G. D., *Br. J Ophthalmol* 46, 513–522 (1962); and Leighton, D. A., *Trans. Ophthalmol. Soc. U.K.* 96: 28–32 (1976)) and that 13–47% of POAG patients have a positive family history (Phelps, C. D. & Podos, S. M., Glaucoma: In Genetic and Metabolic Eye Diseases (ed. Goldberg, M. F.) 237–259 (Little Brown, Boston, 1974); and Francois, *J. Am. J Ophthalmol.* 61, 652–665 (1966)). In addition, there have been reports of the existence of families with clearly heritable open angle glaucoma (Harris, D. *Am. J. Ophthalmol.* 60: 91–95 (1965); Francois, J. *Am. J Ophthalmol.* 61: 652–665 (1966); Waardenbeurg, P. J. *Genetica* 25: 79–129 (1950), Biro, I *Ophthalmologica* 122:228–238 (1951) and Johnson, A. T. et al., *Ophthalmology* 100: 524–529 (1993)).

Although these findings raise the possibility that a significant portion of glaucoma may be genetically determined, prior to the instant invention, a glaucoma causing gene had not been identified.

SUMMARY OF THE INVENTION

The instant invention features a novel glaucoma causing gene which has been isolated to a 2.5 centimorgan region of human chromosome 1. Based on this finding, in one aspect the invention features methods and kits for diagnosing a subject with glaucoma or with a predisposition for developing glaucoma. In a preferred embodiment, the diagnostic methods and kits utilize a set of primers for amplifying regions of the glaucoma causing gene, and means for analyzing the glaucoma causing gene for differences (mutations) from the normal coding sequence. In another embodiment, the diagnostic methods and kits employ antibodies to a glaucoma causing protein (i.e. a protein encoded by the glaucoma gene) in an immunoassay procedure to detect the presence of a glaucoma causing protein in a subject's bodily fluid.

The instant disclosed diagnostic methods allow an ophthamologist to determine whether a presymptomatic individual at risk for developing glaucoma (based on family history) will develop the disease. If the diagnosis is negative, the individual will not have the worry of anticipating development of the disease over time. If the diagnosis is positive, steps may be taken to prevent or ameliorate the effects of the disease before damage, such as loss of vision, occurs.

In another aspect, the invention features a glaucoma correcting gene (i.e. a "normal" gene corresponding to a mutated gene that causes glaucoma). In one embodiment, the invention features therapies for treating or preventing glaucoma in a subject by administering an effective amount of a glaucoma correcting gene into the subject so that a glaucoma correcting protein is expressed in a sufficient amount to compensate for the deficiency of functional protein that results in glaucoma.

In a further aspect, the invention features a glaucoma correcting protein encoded by the gene as well as methods for producing a recombinant form of the glaucoma correcting protein. In one embodiment, the recombinant glaucoma correcting protein is produced in vitro in cell culture. In another embodiment, the protein is produced by a transgenic animal. In another embodiment, the invention features therapies for treating or preventing glaucoma in a subject by administering to the subject an effective amount of a glaucoma correcting protein to compensate for the inability of the subject's glaucoma causing genes to produce glaucoma correcting protein. In a further aspect, the invention features alternative therapies that address the molecular basis for glaucoma. In yet a further aspect, the invention relates to animals expressing the glaucoma causing gene, which may be useful, for example, as animal models for testing drugs for treating glaucoma.

The instant disclosed protein replacement, gene and alternative therapies for treating glaucoma correct the biochemical defect resulting in disease. Therefore the instant disclosed therapies offer a major advance over currently available pharmacological and mechanical glaucoma therapies, which nonspecifically lower intraocular pressure.

Other features and advantages will be readily apparent from the following detailed description and claims.

DETAILED DESCRIPTION OF THE INVENTION

Figure 1:
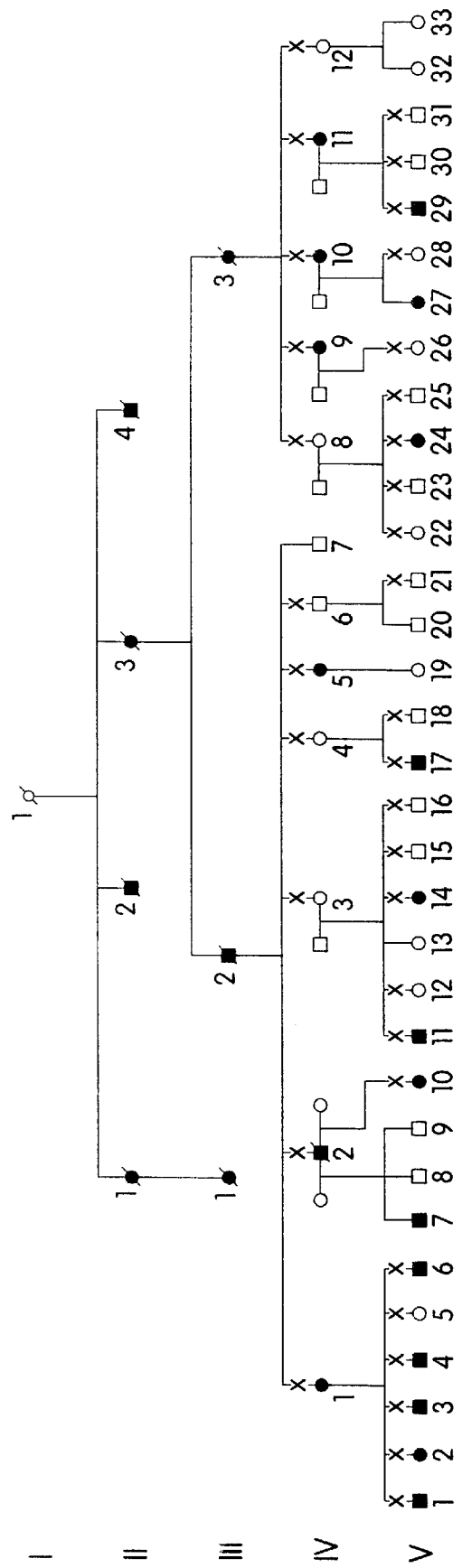
FIG. 1 shows the pedigree of the glaucoma family used in determining linkage of a glaucoma gene to chromosome 1q21-31.

The instant invention is based on linkage studies that have mapped a glaucoma causing gene to a region of human chromosome 1. As described in detail in the attached Example 1, linkage has been determined based on studies performed on a family with an autosomal dominant form of juvenile open angle glaucoma. The pedigree of this family is shown in FIG. 1. Of the thirty seven family members, nineteen were found to be affected based on findings of elevated intra-ocular pressure, optic nerve cupping and visual field loss. Three additional patients were considered to be affected on the basis of mildly elevated intra-ocular pressures and an obviously affected offspring. This family was used for linkage analysis with short tandem repeat polymorphisms (STRPs) (Weber, J. L. and P. E. May (1989) Am. J. Hum. Genet 44:388–396; Litt, M. and J. A. Luty (1989) Am. J. Hum. Genet. 44:397–401; Weber, J. L. (1990) Genomics 7:524–530). The STRPs used were distributed across the entire genome. The family members were genotyped with over 90 STRPs before linkage was detected with markers that map to chromosome 1q. A total of 33 chromosome 1 markers were typed in this family and significant linkage to eight STRPs was demonstrated. The glaucoma locus was initially mapped to a 20 centimorgan (cM) region flanked by markers D1S191 and LAMB2 located in the region of 1q21-q31. Pairwise linkage analysis using marker D1S212 resulted in a lod score of 6.5 ($\theta$=0). Since this marker was fully informative in the family, multipoint analysis with other linked markers did not add to the peak lod score obtained with marker D1S212.

Figure 2:
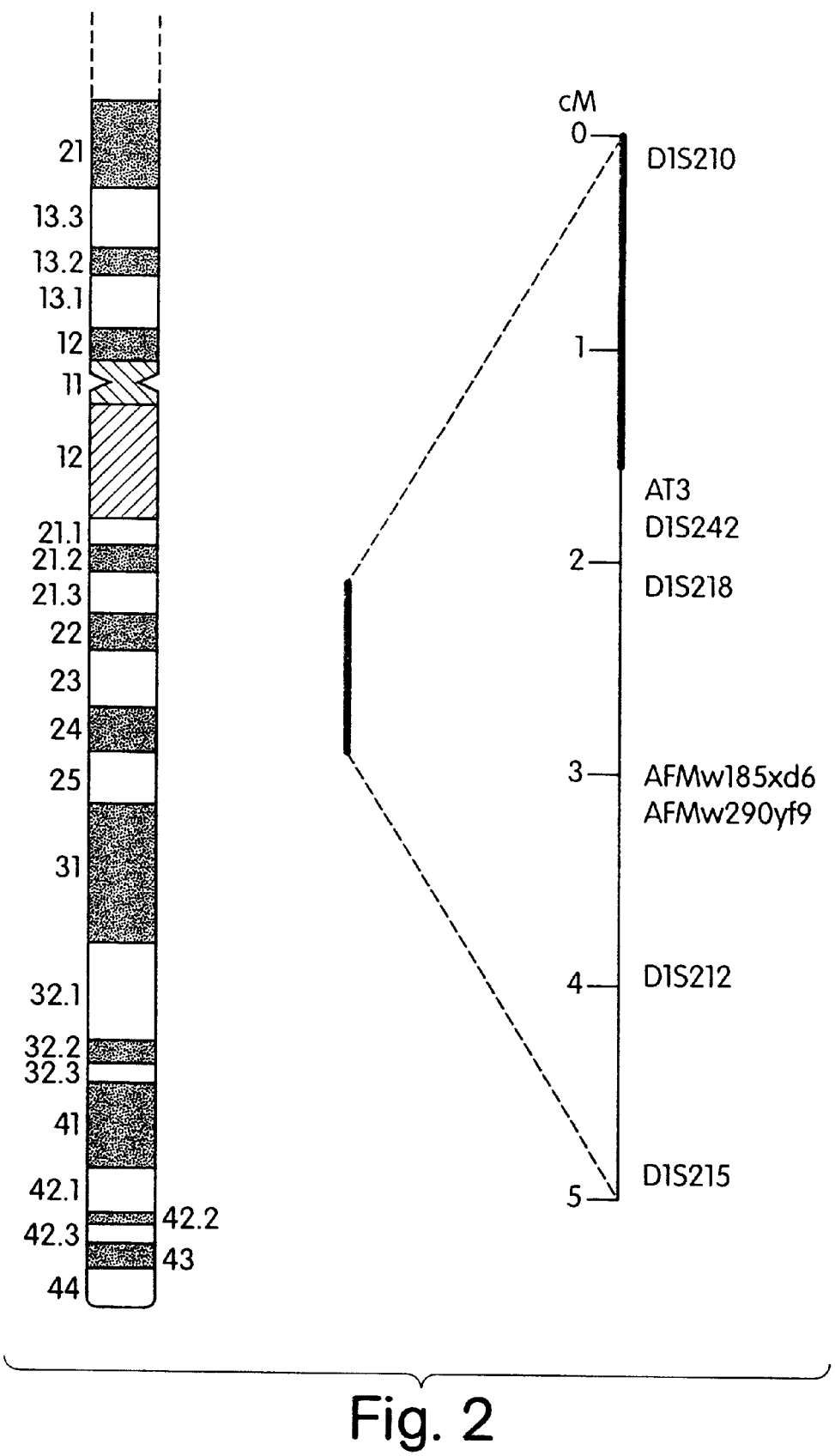
FIG. 2 is a map of human chromosome 1q showing relative positions of markers linked to a glaucoma causing gene.

A second large branch of the original family and two independent large juvenile glaucoma families were subsequently identified. Chromosome 1q linkage has been demonstrated in all three families. The additional meioses in the original family and one of the new families were used to narrow the candidate interval to an approximate 2.5 cM interval between markers D1S210 and AT3 as shown in FIG. 2. Primary linkage data has confirmed linkage at 1q in a large Michigan pedigree. All classic juvenile primary open angle glaucoma pedigrees tested to date (including a French-Canadian pedigree) appear to map to this locus, indicating that this locus is a major juvenile primary open angle glaucoma locus.

Figure 3:
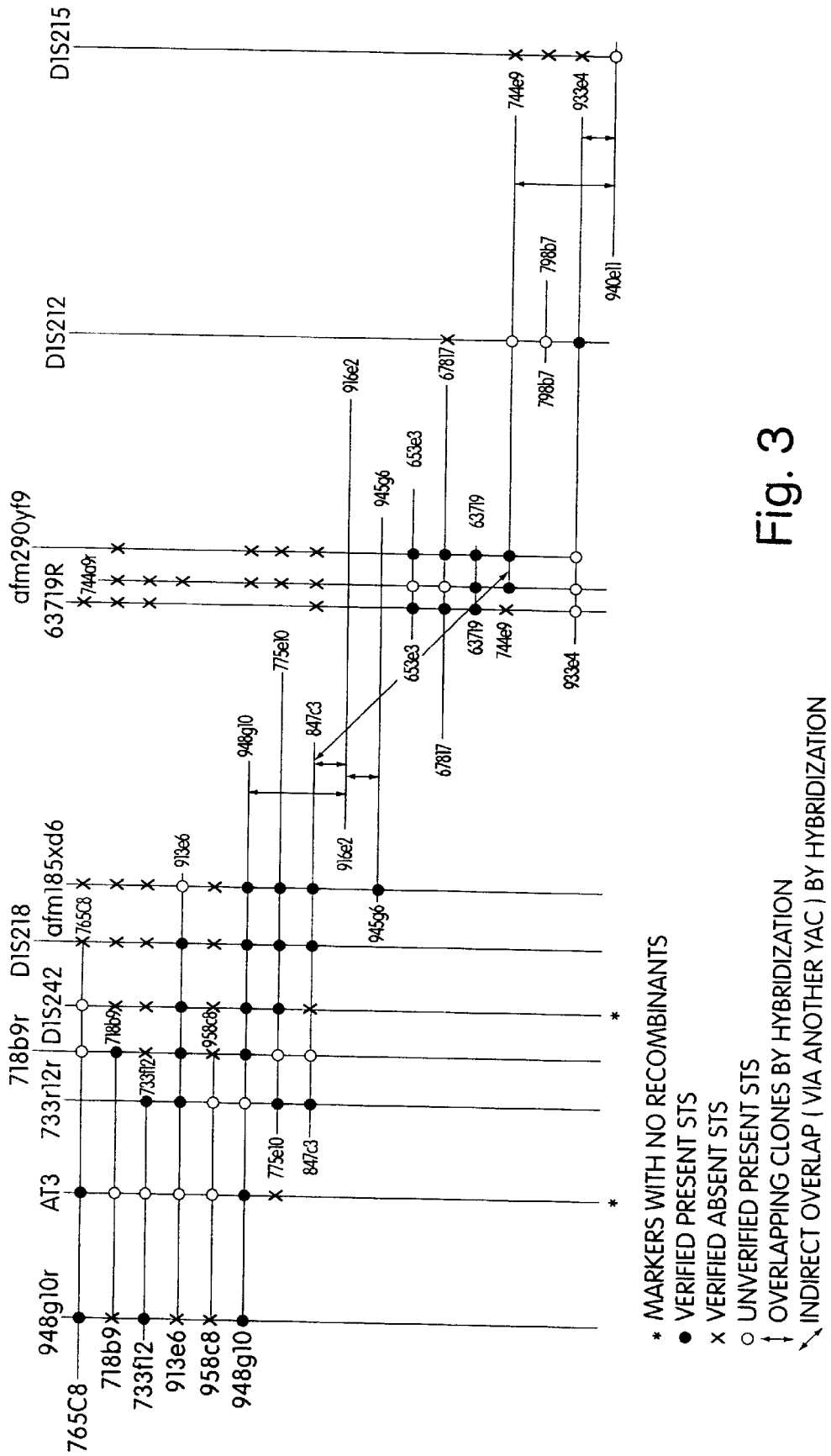
FIG. 3 is a graphic representation of a Yeast Artificial Chromosome (YAC) contig of the 1q glaucoma region.

In addition to genetic mapping, CEPH YAC and mega YAC libraries have been screened with the flanking markers and markers that show no recombination with the disease. Further, a YAC contig across the candidate interval has been generated and is shown in FIG. 3.

The linkage of primary open angle glaucoma to 1q21-q31 suggested a reasonable candidate gene for this disorder. The gene for atrial natriuretic peptide receptor A (ANPR-A) has been mapped by in situ hybridization to 1q21-q22 and has been shown to be expressed in the eye (Lowe, D. G. et al (1990) Genomics 8:304–312). In human studies, atrial natriuretic peptide (ANP) has been shown to decrease intra-ocular pressure, indicating that a defect in the receptor for ANP could lead to increased pressure (Diestelhorst, M. (1989) Int Ophthalmol 13:99–101). However, a polymorphism has recently been identified in the ANPR-A gene and demonstrated recombination events between this gene and the glaucoma locus. This effectively excludes involvement of the gene for atrial natriuretic peptide receptor A as causing glaucoma.

Another reasonable candidate gene which lies within this linkage region is the laminin B2 (LAMB2) gene. A highly informative STRP has been reported within this gene. Genotyping in the juvenile onset glaucoma family demonstrated multiple recombinants with the disease phenotype and therefore excludes LAMB2 as a candidate gene.

Isolation of a glaucoma causing gene makes glaucoma testing a reality. Diagnostic testing can now be performed on presymptomatic individuals, who are at risk of developing glaucoma based on family history. In addition, tests can be performed on postsymptomatic individuals diagnosed with glaucoma based on an ophthamologic examination. Further a diagnostic test could be performed on DNA obtained from a fetus in utero, although glaucoma would not to appear to be a sufficiently life threatening or diabling disease to warrant prenatal identification.

Glaucoma testing can be performed on a nucleic acid sample obtained from a subject by standard techniques. For example a patient's bodily fluid (e.g. blood) can be obtained by known techniques (e.g. venipuncture). Alternatively, nucleic acid tests have been performed on dry samples (e.g. hair or skin). Fetal nucleic acid samples can be obtained from maternal blood as described in International Patent Application No. WO91/07660 to Bianchi; alternatively amniocytes or chorionic villi may be obtained for performing prenatal testing.

It may be useful or essential to first amplify the complement of nucleic acid present in a sample prior to analysis using one of many possible means. For example, the nucleic acid may be amplified using a procedure such as the polymerase chain reaction (PCR) (Saiki R. et al., (1988) Science 239:487–49; Sheffield, V. C. et al., (1989) Proc. Natl. Acad. Sci. U.S.A. 86: 232–236); or Q-beta replicase.

A variety of methods for analyzing a fragment of nucleic acid for the presence of a glaucoma causing gene are available in the art. Because it is likely that more than one mutation may result in a glaucoma phenotype (as has been found to be the case with other genetic diseases such as cystic fibrosis), a preferred method for diagnosing glaucoma can simultaneously detect the presence of a number of different mutations, examples of such methods include denaturing gradient gel electrophoresis (Sheffield, V. C. et al., (1989) *Proc. Natl. Acad. Sci USA* 86:232–236 and mobility shift analysis (Orita, M. et al., (1989) *Proc. Natl. Acad. Sci USA* 86:2766–2770.) Alternatively, a sample may be analyzed for the presence of a glaucoma gene by detecting hybridization with a nucleic acid fragment or oligonucleotide probe (i.e. a nucleic acid fragment or oligonucleotide antisense to a glaucoma gene that has been labelled e.g. radioactively with isotopes (e.g. $^{32}$P) or nonradioactively with tags such as biotin, which can be labelled for example upon reaction with fluorescent avidin or streptavidin (Wallace et al., (1986) *Cold Spring Harbour Symp. Quant. Biol.* 51:257–261); direct sequencing (Church and Gilbert, (1988) *Proc. Nat. Acad. Sci. U.S.A.* 81:1991–1995; Sanger, F. et al., (1977) *Proc. Nat. Acad Sci.,* 74:5463–5467; Beavis et al., U.S. Pat. No. 5,288,644), restriction enzyme analysis (Flavell et al., (1978) *Cell* 15:25; Geever et al., (1981) *Proc. Nat. Acad. Sci. U.S.A.* 78:5081; Orita, M et al., *Proc. Natl. Acad. Sci. U.S.A.* 86: 2766–2770 (1989)), RNAse protection (Myers, R. M., et al., (1985) *Science* 230:1242), chemical cleavage (Cotton et al., (1985) Proc. Nat. Acad. Sci. U.S.A. 85:4397–4401) and the ligase mediated detection procedure (Landegren et al., (1988) *Science* 241:1077).

Alternatively, glaucoma can be diagnosed by detecting the presence of a glaucoma causing gene product (i.e. a glaucoma causing protein, polypeptide or peptide) in a sample obtained from a subject using standard immunoassay procedures (David et al., U.S. Pat. No. 4,376,110). Polyclonal or monoclonal antibodies specific to a glaucoma causing gene product can be generated using standard techniques (e.g., Kohler and Milstein, (1975) Nature 256: 495–497; Olsson and Kaplan, (1980) Proc. Natl. Acad. Sci. (USA) 77:5429). Alternatively recombinant immunoglobulins can be generated using standard techniques (Cabilly et al., U.S. Pat. No. 4,816,567)

In addition to being used diagnostically, isolation of a glaucoma gene allows production of transgenic animals expressing a glaucoma gene. These animals can be used in developing drugs for treating glaucoma.

In addition, isolation of a glaucoma gene allows identification of a glaucoma correcting gene (i.e. a "normal" gene corresponding to the mutated gene that expresses a glaucoma causing gene product which results in glaucoma). Identification of a glaucoma correcting gene and protein (e.g. glycosylated or unglycosylated protein, polypeptide or protein makes protein replacement and gene therapy treatments for glaucoma possible.

A glaucoma correcting protein can be made by introducing (preferably in a suitable expression cassette, containing an appropriate promoter and optional enhancer sequence) into cells in culture using standard techniques (e.g., via calcium phosphate or calcium chloride co-precipitation, DEAE dextran mediated transfection, lipofection, or electroporation). Recombinant cells encoding the glaucoma correcting gene can then be cultured in vitro in a manner that allows expression and preferably also secretion, and the recombinant factor can be purified using well known techniques. Either prokaryotic or eukaryotic cells may be useful "host cells" for producing recombinant glaucoma correcting protein in vitro. Preferred host cells are mammalian cells (e.g., COS, Baby hamster kidney (BHK) and C127 cells), yeast cells and insect cells.

As an alternative to production by in vitro culture, recombinant glaucoma correcting protein can also be produced in vivo, for example in a transgenic animal. Preferably in vivo production is carried out in a manner that is not detrimental to the animal host. Transgenic methods for producing recombinant proteins are well known in the art and include for example using gene constructs, which include a milk protein specific promoter for production and secretion in mammalian milk (see e.g., U.S. Pat. No. 4,873,316 entitled "Isolation of Exogenous Recombinant Proteins From The Milk of Transgenic Mammals" to Meade et.al.).

It may be advantageous to use a functional fragment or derivative of the glaucoma correcting protein, for example in developing an appropriate pharmaceutical composition or for generating antibodies. Various fragments and derivatives can be tested for biological activity (i.e., ability to prevent glaucoma symptoms) using an appropriate activity assay. In addition, variously glycosylated forms of a glaucoma correcting protein can be tested for example for increased circulatory life using an appropriate activity assay.

A subject (e.g. a human or animal) can be treated for glaucoma by administration of an "effective amount" of a glaucoma correcting protein alone or in conjunction with a pharmaceutically acceptable carrier or diluent according to any method that allows access into a subject's blood stream and enables contact with the subject's eye tissue. An effective amount is an amount sufficient to reduce or eliminate the symptoms associated with glaucoma. The effective amount can be determined by one of skill in the art using no more than routine experimentation and may take into account such factors as the type and severity of symptoms being treated, the weight and/or age of the subject, the previous medical history of the subject, and the selected route for administration. Exemplary modes of administration include topically, intraocularly, subcutaneously, intravenously, intraperitoneally, intramuscularly, parenterally, submucosally, orally, transdermally or other appropriate manner. If necessitated by a particular mode of administration, a glaucoma correcting protein can be encapsulated within a material that protects it from enzymatic degradation.

Alternatively, a preparation of a glaucoma correcting gene can be incorporated into a suitable vector for delivering the gene to appropriate cells in a subject suspected or known to have glaucoma. Since glaucoma is a disorder affecting the optic nerve, gene therapy vectors preferably are capable of delivering a glaucoma correcting gene to the subject's optic nerve into a subject's stem cells. For use in clinical treatment, appropriate vectors must also be appropriately maintained in host cells and be safe. Preferred vectors for performing gene therapy include retrovirus, adenovirus, adeno-associated virus and lipid based vectors.

A subject can be treated by administration of an "effective amount" of a glaucoma correcting gene alone or in conjunction with a pharmaceutically acceptable carrier or diluent according to any method that allows access to a subject's eye tissue. An "effective amount" of a glaucoma correcting gene is an amount sufficient to result in manufacture of sufficient glaucoma correcting protein to reduce or eliminate the symptoms associated with glaucoma. The effective amount can be determined by one of skill in the art using no more than routine experimentation and may take into account such factors as the type and severity of symptoms being treated, the weight and/or age of the subject, the previous medical history of the subject, and the selected route for administration. Exemplary modes of administration of a glaucoma correcting gene therapy vector include topically, intraocularly, subcutaneously, intravenously, intraperitoneally, intramuscularly, parenterally, submucosally, orally, transdermally or other appropriate manner. If necessitated by a particular mode of administration, a glaucomal correcting gene can be encapsulated within a material that protects it from enzymatic degradation.

In addition to the gene and protein replacement therapies described above, alternative therapies can be developed that prevent or compensate for a step along the biochemical that results in glaucoma. The identification of a single gene known to be responsible for a specific disease (here juvenile onset open angle glaucoma) can also improve understanding of the types and classes of genes that can cause related disorders (e.g. other types of glaucoma). For example, most investigators predicted that the genes causing macular degeneration would be expressed in the retinal pigment epithelium (RPE) because it is this tissue that shows the earliest observable sign of disease. However, there is now indication that an abnormal RDS/peripherin gene product, which is a component of photoreceptors, can cause macular disease (Nichols, B. E. et al., (1992) *Nature Genetics* 3:202–207; Wells, J. J. et al., (1992) *Nature Genetics* 3:213–217).

In addition, the identification of one gene product causing a disorder can make it possible to identify other genes which can cause a similar phenotype. For example, the identification of the dystrophin gene has led to the isolation of dystrophin related glycoproteins, at least one of which plays a role in other forms of muscular dystrophy. Also, a gene capable of causing a Mendelian disorder, may contribute to the inheritance of a multifactorial form of the disorder. A striking example of this has been the identification of genes involved in various forms of cancer (e.g. colon cancer) by studying familial forms of cancer (e.g. hereditary nonpolyposis colon cancer and familial adenomatous polyposis). Groden, J. A. et al., (1991) *Cell* 66:589–600 ; Aaltonen, L. A. (1993) *Science* 260:812–816). It is possible that juvenile open angle glaucoma is allelic to some fraction of adult onset primary open angle glaucoma and/or that alleles of the juvenile gene contribute to the portion of adult open angle glaucoma that has a multifactorial etiology.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Genetic Linkage of Familial Open Angle Glaucoma to Chromosome 1q21-q31

Pedigree

A family in which five consecutive generations have been affected with juvenile-onset, open-angle glaucoma without iridocorneal angle abnormalities was identified. The family comprised descendants of a woman who emigrated from Germany to the midwestern United States in the late 1800s. The disease state in affected family members included onset during the first 3 decades of life, normal anterior chamber angles, high intraocular pressures, lack of systemic or other ocular abnormalities, and need for surgery to control the glaucoma in affected individuals. A total of 35 family members at 50% risk for glaucoma had complete eye examinations including visual acuity with refraction, slit-lamp biomicroscopy, applanation tomometry, gonioscopy, stereo disc photography and Humphrey, Goldmann or Octopus perimetry. Two other affected patients were ascertained by reviewing records of other opthalmologists. Patients were considered to be affected for linkage if they had documented pressures greater than 30 mm Hg and evidence of optic nerve or visual field damage; or, if they had intraocular pressures greater than 22 mm Hg and an obviously affected child. Affected family members are characterized by an early age of diagnosis, a normal appearing trabecular meshwork, very high intraocular pressures (often above 50 mm Hg), and relatively pressure-resistant optic nerves. FIG. 1 is a pictorial representation of the pedigree.

DNA Typing

Blood samples were obtained from all living affected family members as well as six spouses of affected patients with children. 10 ml blood were obtained from each patient in EDTA-containing glass tubes. DNA was prepared from the blood using a non-organic extraction procedure (Grimberg, J. et al. Nucl. Acids Res 17, 8390 (1989)). Short tandem repeat polymorphisms (STRPs) distributed across the entire autosomal genome were selected from the literature or from those kindly provided by J. L. Weber. The majority were [dC-dA]-[dG-dT] dinucleotide repeats. Oligonucleotide primers flanking each STRP were synthesized using standard phosphoramidite chemistry (Applied Biosystems model 391 DNA synthesizer). Amplification of each STRP was performed with 50 ng. of each patient's DNA in a 8.35 $\mu$l PCR containing each of the following: 1.25 $\mu$l 10 X buffer (100 mM Tris-HCl pH 8.8, 500 mM KCl, 15 mM MgCl$_2$, 0.01% w/v gelatin), 300 $\mu$M each of dCTP, dGTP and dTTP, 37 $\mu$M DATP, 50 pmoles each primer, 0.25 $\mu$l $\alpha$-$^{35}$S-dATP (Amersham, >1000 Ci mmol$^{-1}$), and 0.25 U Taq polymerase (Perkin-Elmer/Cetus). Samples were incubated in a DNA thermocycler (Perkin-Elmer/Cetus) for 35 cycles under the following conditions: 94° C. for 30 s, 55° C. for 30 s, and 72° C. for 30 s. Following amplification, 5 $\mu$l of stop solution (95% formamide, 10 mM NaOH, 0.05% Bromophenol Blue, 0.05% Xylene Cyanol) was added to each sample. Following denaturation for 3 min at 95° C., 5 $\mu$l of each sample was immediately loaded onto prewarmed polyacrylamide gels (6% polyacrylamide, 7 M urea) and electrophoresed for 3–4 h. Gels were then placed on Whatman, 3 mm paper and dried in a slab gel dryer. Autoradiographs were created by exposing Kodak Xomat AR film to the dried gels for 24–36 h.

Linkage Analysis

Genotypic data from the autoradiographs were entered into a Macintosh computer. A Hypercard-based program (Nichols, B E et al., Am J Hum Genet 51 A369 (1992)) was used to store and retrieve marker data as well as to export it to a DOS-compatible machine for analysis with the computer program LINKAGE (version 5.1) (Lathrop, G M and LaLouel, J M 359, 794–801 (1992)). Allele frequencies were assumed to be equal for each marker. The MLINK routine was used for pairwise analysis. The relative odds of all possible orders of the disease and two markers (D1S191 and D1S194) was performed under the ILINK program. Significance of linkage was evaluated using the standard criterion ($Z_{max}$>3.0).

Results

Clinical Findings

All of the 37 family members studied were at 50% risk of having the disease because of a known affected parent or sibling. Nineteen of these patients had elevated intraocular pressures and visual field defects consistent with the diagnosis of primary open angle glaucoma. Three more patients had moderately elevated intraocular pressures and obviously affected children.

Linkage Analysis

Over 90 short tandem repeat polymorphisms were typed in the family before linkage was detected with markers that map to the long arm of chromosome 1. Two-point maximum likelihood calculations using all available family members and 33 chromosome 1 markers revealed significant linkage to eight of them (Table 1). D1S212 was fully informative for all affected members of the family, and pairwise linkage analysis produced a lod score of 6.5 (θ=0). Multipoint linkage analysis did not add to the peak lod score. The glaucoma locus was therefore determined to be located in a region of about 20 centimorgans (cM) in size between D1S191 and D1S194. Both of these markers demonstrated multiple recombinants (two and three, respectively) in affected individuals in the family. The order D1S191-glaucoma-D1S194 was more than 1,000 times more likely than the other two possible orders.

6) Denature samples at 95° C. for 3 minutes and load immediately onto a prewarmed polyacrylamide gel.
7) Dry gels on Whatmann paper and expose autoradiography film for 1–2 days.

Where possible, multiple loadings of different STRPs on gels were performed. Up to 6 markers per gel have been successfully loaded. In addition, the PCR amplification (up to three markers) have been successfully multiplexed. The juvenile glaucoma gene is believed to lie between markers AFM238 and AT3 (an 8 centimorgan interval) based on observed recombinations within the families studied. Hyplotypic analysis between families has further narrowed this interval to the 2 centimorgan interval between D1S210 and AT3.

TABLE 1

Pairwise linkage data

| | \multicolumn{7}{c}{Recombination fraction} | | | | |
|---|---|---|---|---|---|---|---|---|---|---|
| | 0.05 | 0.19 | 0.15 | 0.20 | 0.25 | 0.30 | 0.40 | $Z_{max}$ | θ | Locus | Reference |
| D1S212 | 6.0 | 5.4 | 4.8 | 4.2 | 3.6 | 2.9 | 1.4 | 6.5 | 0.00 | 1 | 35 |
| D15215 | 5.1 | 4.6 | 4.0 | 3.5 | 2.9 | 2.3 | 1.0 | 5.6 | 0.00 | 1 | 35 |
| D15218 | 4.7 | 4.3 | 3.8 | 3.3 | 2.7 | 2.2 | 1.0 | 5.2 | 0.00 | 1 | 35 |
| D1S238 | 4.4 | 4.2 | 3.9 | 3.4 | 2.9 | 2.4 | 1.2 | 4.4 | 0.04 | 1 | 35 |
| D1S117 | 3.8 | 3.6 | 3.3 | 2.8 | 2.3 | 1.8 | 0.7 | 3.8 | 0.04 | 1q | 36 |
| D1S104 | 3.2 | 2.9 | 2.6 | 2.3 | 2.0 | 1.6 | 0.7 | 3.4 | 0.00 | 1q21–q23 | 37 |
| D1S191 | 3.0 | 3.2 | 3.0 | 2.7 | 2.4 | 1.9 | 0.9 | 3.2 | 0.09 | 1 | 35 |
| D1S196 | 2.9 | 2.6 | 2.3 | 2.0 | 1.6 | 1.3 | 0.5 | 3.1 | 0.00 | 1 | 35 |

EXAMPLE 2

Genetic Fine Mapping of the Juvenile Primary Open Angle Glaucoma Locus and Identification and Characterization of a Glaucoma Gene Once primary linkage has been identified, the next step in identifying any disease gene by positional cloning is the narrowing of the candidate locus to the smallest possible genetic region. The initial study described in Example 1 demonstrated that a primary open angle glaucoma gene lies within an approximately 20 cM region flanked by markers D1S194 and D1S191 on chromosome 1q. Additional markers and families were obtained and used to refine the genetic locus to a 2.5 cM region using two of these families. The third family should allow the interval to be further narrowed.

In addition to the family resources, polymorphic DNA markers and genetic maps were used to refine the 1q glaucoma locus. Using STRPs, the genotype of each family member was determined. Amplification of each STRP was performed using the following protocol:

1) Dilute genomic DNA (about 1 μg/μl) 1/50 i.e. 20 μl "stock" DNA and 980 dd H$_2$O.
2) Use 2.51 μl of "dilute" DNA as template for PCR
3) Prepare PCR reaction mix as follows:
   1.25 μl 10 X Buffer (Stratagene)
   0.12 μl of each primer (50 pmoles each primer)
   0.5 μl dNTPs (5 mM C,T,&G and 0.625 mM A "cold")
   3.5 μl dd H$_2$O
   0.25 μl $^{35}$S-dATP
   0.1 μl Taq polymerase
   oil (one drop)
4) Perform PCR at optimal conditions for given primers (usually 94° 30 s, 55° 30 s and 72° 30 s) and run for 35 cycles.
5) Add 5 μl stop solution (95% formamide, 10 mM NaOH, 0.05% bromophenol blue, 0.05% xylene cyanol) to each tube.

Since the genetic interval has been narrowed significantly physical mapping strategies can be used. The closest flanking markers to screen total human genomic yeast artificial chromosome (YAC) libraries to identify YACs mapping to the region of interest. The CEPH and CEPH mega-YAC libraries can be used for this purpose (available from the Centre d'Etude du Polymorphisme Humain (CEPH) Paris, France). Forty-four percent of the clones in the CEPH mega-YAC library have an average size of 560 kb, an additional 21% have an average size of 800 kb, and 35% have an average size of 120 kb. This library is available in a gridded micro-titer plate format such that only 50–200 PCR reactions need to be performed using a specific sequence tagged site (STS) to identify a unique YAC containing the STS. The YAC contigs identified by CEPH have been used to begin constructing a contig across the 1q candidate region (see FIG. 3). YAC contigs using YAC ends can be constructed to identify additional YACs. YAC ends can be rescued using anchored PCR (Riley, J. et al (1990) *Nucleic Acids Res* 18:2887–2890), the ends can then be sequenced and the sequence can be used to develop a sequence tagged site (STS). The STS can be used to rescreen the YAC library to obtain an overlapping adjacent YAC.

Because some YACs have been shown to be chimeric or to contain deletions or rearrangements, particularly those from the mega YAC library, the correctness of each YAC contig should be verified by constructing a pulse field map of the region. In addition, chimeric YACs are minimized by ensuring that the YAC maps to a single chromosome by fluorescent in situ hybridization (FISH) or that the two YAC ends map to the same chromosome using monochromosomal somatic cell hybrids (NIGMs Panel 2). In addition, the YAC chimera problem can be minimized by not relying on any single YAC to span a given chromosome segment, but rather by obtaining at least two overlapping independent YACs to ensure coverage of a given region.

Once a YAC contig spanning the candidate region has been isolated, this reagent can be used to generate additional genetic markers for potentially finer genetic mapping. In addition, the YACs can be used to make higher resolution physical mapping reagents such as region specific lambda and cosmid clones. Lambda and cosmid clones can be used for isolation of candidate genes. A modification of "exon trapping" (Duyk, G. M. (1990) *Proc Natl Acad Sci USA* 87:8995–8999) known as exon amplification (Buckler, A. J. (1991) *Proc Natl Acad Sci USA* 88:4005–4009) can be used to identify exons from genes within the region. Exons trapped from the candidate region can be used as probes to screen eye cDNA libraries to isolate cDNAs. Where necessary, other strategies can be utilized to identify genes in genomic DNA including screening cDNA libraries with YAC fragments subcloned into cosmids, zoo blot analysis, coincidence cloning strategies such as direct selection of cDNAs with biotin-streptavidin tagged cosmid clones (Morgan, J. G. et al (1992) *Nucleic Acid Res* 20 (19) :5173–5179), and HTF island analysis (Bird, A. P. (1987) *Trends Genet* 3:342–247). Promising genes will be further evaluated by searching for mutations using GC-clamped denaturing gradient gel electrophoresis (Sheffield, V. C. et al (1989) *Genomics* 16:325–332), single strand conformational gel polymorphism (SSCP) analysis (Orita, M. et al (1989) *Proc Natl Acad Sci USA* 86:2766–2770) and direct DNA sequencing.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. A method for diagnosing a subject having glaucoma or having a predisposition to developing glaucoma, said subject having family members diagnosed with glaucoma, comprising the steps of:
    a) obtaining a nucleic acid containing sample from a subject;
    b) amplifying the nucleic acid with primers which amplify a region of human chromosome 1 corresponding to a polymorphic marker selected from the group consisting of D1S191, D1S194, D1S196, D1S212, D1S210, D1S215, D1S218, D1S238, D1S117, D1S104, LAMB2, AFM238 and AT3; and
    c) analyzing the amplification product to determine the presence of a polymorphism indicative of an allele type linked to glaucoma.
2. The method of claim 1, wherein said marker is D1S191.
3. The method of claim 1, wherein said marker is D1S194.
4. The method of claim 1, wherein said marker is D1S196.
5. The method of claim 1, wherein said marker is D1S212.
6. The method of claim 1, wherein said marker is D1S215.
7. The method of claim 1, wherein said marker is D1S218.
8. The method of claim 1, wherein said marker is D1S238.
9. The method of claim 1, wherein said marker is D1S117.
10. The method of claim 1, wherein said marker is D1S104.
11. The method of claim 1, wherein said marker is LAMB2.
12. The method of claim 1, wherein said marker is AFM238.
13. The method of claim 1, wherein said marker is AT3.
14. The method of claim 1, wherein said nucleic acid is analyzed for the presence of short tandem repeat polymorphisms (STRPs).
15. The method of claim 1, wherein said markers define a 2.5 cM interval between markers D1S210 and AT3 in the region of human chromosome 1.
16. The method of claim 1, wherein said glaucoma is juvenile open angle glaucoma or adult primary open angle glaucoma.
17. The method of claim 1, wherein said subject is an adult human.
18. The method of claim 1, wherein said subject is a human fetus in utero.
19. The method of claim 1, wherein said marker is D1S210.

* * * * *